United States Patent [19]

Alter

[11] Patent Number: 4,586,604
[45] Date of Patent: May 6, 1986

[54] CULTURE COLLECTION INSTRUMENT AND SEALED SWAB HOLDER THEREFOR

[75] Inventor: Richard R. Alter, Delavan, Wis.

[73] Assignee: Continental Plastic Corporation, Delavan, Wis.

[21] Appl. No.: 626,210

[22] Filed: Jun. 28, 1984

[51] Int. Cl.⁴ .................. A61D 10/00; B65D 81/24
[52] U.S. Cl. .................... 206/210; 128/756; 128/759; 206/209; 206/363; 435/295; 604/1; 604/171; 604/199
[58] Field of Search ............ 206/210, 209, 15.2, 206/361, 209.1, 363, 364; 128/759, 749, 756; 435/292, 295; 604/187, 197, 199, 1, 171, 172

[56] References Cited

U.S. PATENT DOCUMENTS

| 2,218,738 | 10/1940 | Boysen | 206/361 X |
| 2,902,146 | 9/1959 | Doherty | 206/363 X |
| 3,050,060 | 8/1962 | Hoffman | 604/187 X |
| 3,203,545 | 8/1965 | Grossman | 206/210 |
| 3,513,830 | 5/1970 | Kalayjian | 128/759 |
| 3,800,781 | 4/1974 | Zalucki | 128/749 |
| 4,014,746 | 3/1977 | Greenspan | 128/759 X |
| 4,023,559 | 5/1977 | Gaskell | 128/759 |
| 4,457,313 | 7/1984 | Alter | 128/759 |

FOREIGN PATENT DOCUMENTS

WO80/01353  7/1980  PCT Int'l Appl.
2059992     4/1981  United Kingdom ......... 435/292

Primary Examiner—William Price
Assistant Examiner—Bryon Gehman
Attorney, Agent, or Firm—Emrich & Dithmar

[57] ABSTRACT

A culture collection instrument for use in animal husbandry includes a tubular swab holder adapted to receive an elongated rod having a swab element on its end and a tubular swab protector adapted to receive and hold the tubular swab holder. The tubular swab protector includes a scored portion thereon a predetermined distance from the end of the swab protector such that flexing of the swab protector predeterminely breaks the swab protector and swab element from the elongated rod to provide a sealed tubular holder for the cultured swab element.

9 Claims, 8 Drawing Figures

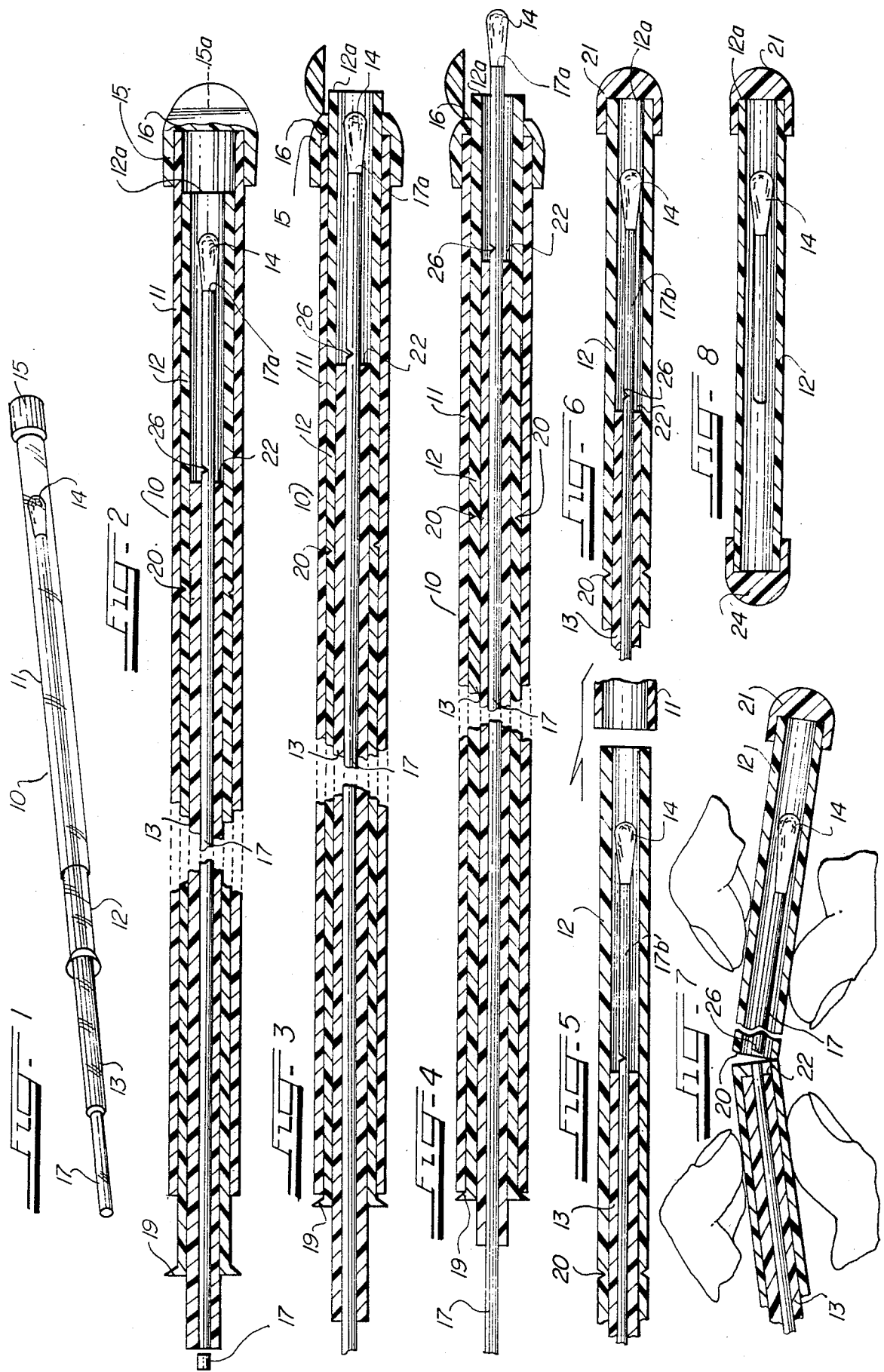

CULTURE COLLECTION INSTRUMENT AND SEALED SWAB HOLDER THEREFOR

BACKGROUND OF THE INVENTION

The present invention relates to a novel culture collection instrument useful in medication, antiseptic and culture collection processes utilized in the animal husbandry industry. The present application is related to now pending U.S. Pat. No. 4,457,313, entitled SHIELD PROTECTOR FOR ARTIFICIAL INSEMINATION AND CULTURE COLLECTION INSTRUMENTS, filed in the name of the present inventor on Apr. 23, 1982, and assigned to the assignee of the present invention.

During the insertion of a culture collection instrument into the cervix of an animal, the instrument must first pass through the vulva and/or cervical canal of the animal. Because the vulva and cervical canal are not sterile and, generally, contain bacteria or diseased germs, such as vaginal or uterine infections or microplasa, it is important to eliminate the transfer of these diseased germs or microplasa into the cervix. Additionally, because the insertion of the culture collection control instrument must pass through the cervical canal, often times the prior art devices have carried and transported the disease germs and contaminants from the cervical canal into the cervix during the cultural collection process. Also, such prior art devices do not provide means by which upon removal of the swab element of the cultural collection instrument from the cervix, the swab element may be isolated and sealed thereby preventing further contamination prior to testing and evaluation of the swab element.

Prior art attempts to eliminate the transferral of contaminants and disease from the vulva onto the cultural collection device and to eliminate contamination of the cultural collection instrument during the passage through and into the cervical canal are disclosed in Hoffman U.S. Pat. No. 3,050,060, Kalayjian U.S. Pat. No. 3,513,830 and International Publication No. WO80/01353. However, in each of these prior art devices, no structure is provided in the culture collection instrument for providing a protected and sanitary environment for the the swab portion or element of the culture collection instrument for subsequent analysis and/or tests of the swab element. Additionally, such instruments require manual handling of the swab portion of the culture collection device which can result in contamination of the same and effect the culture collection process of the instrument. Thus, such instruments have not solved the problem of handling the swab portion or element of the culture collection instrument upon removal of the same from the cervix or other interior of the animal and to maintain the swab portion thereof in an isolated and readily identifiable container for subsequent handling of the collected swab portion for transport to the analysis instrument while protecting the swab portion in a sanitary manner from contamination and other impurities.

SUMMARY OF THE INVENTION

An object of the present invention to provide a culture collection instrument which isolates and protects the swab portion of the cultural collection device upon its removal of the instrument from the interior of the body or the cervix of an animal and to sealingly retain the swab element for subsequent handling and transport to the medical analysis station.

In one embodiment of the present invention a shield protector element is sealingly mounted to a culture collection instrument, such protector element or means being described in my copending application Ser. No. 371,208. The cultural collection instrument includes a shield protector element sealingly mounted to the distal end of the outer sheath protector housing which contains a slideable and moveable inner tubular swab protector which contains a slideably mounted swab or culture collection element. Upon insertion of the cultural collection instrument into the animal past the vulva lining, the cervical canal and into the cervix of the animal, the shield protector element eliminates disease and contaminants in the vulva lining from being passed into the cervix and prevents contamination of the cultural gathering or swab tip contained in the cultural collection instrument. When the cultural collection instrument is fully inserted into the cervix of the animal, the inner tubular swab protector portion, having the swab or cultural collection element therein, engages the scored end portion of the shield protector to break away the protected scored end of the shield protector to permit the swab or culture element to move forward with respect to the inner tubular swab protector to culture the animal and/or apply medication to the cervix of an animal.

Upon completion of this medication or cultural collecting process, the swab element is moved outwardly relative to the inner swab protector portion to rest within the outer tubular sheath protector housing, at which time the entire cultural collection instrument is removed from the cervix of the animal. The inner tubular swab protector element and the elongated rod and swab element therein is withdrawn from the outer sheath protector housing and the distal end of the inner tubular swab protector element is capped to seal the same and protect the swab element contained therein. The inner tubular swab protector element includes a scored portion therearound intermediate the distal end thereof. Upon the further withdrawal of the inner tubular swab holder element beyond the scored portion of the inner tubular swab protector element, flexing of the inner tubular swab protector element readily separates and breaks the inner tubular swab protector element and the swab rod intermediate the element to provide a tubular enclosure which when capped on the broken ends thereof, provides a sealed and sanitary holder for the swab element to permit subsequent medical testing of the swab element.

DESCRIPTION OF THE DRAWINGS

FIG. 1 is a perspective view of the cultural collection instrument in accordance with the present invention;

FIG. 2 is a longitudinal cross-sectional view of the cultural collection instrument in accordance with the present invention during insertion of the device into the cervical canal of an animal;

FIG. 3 is a longitudinal cross-sectional view of the cultural collection instrument in accordance with the present invention showing the scored portion of the shield protector element broken away upon engagement by the inner tubular swab protector element;

FIG. 4 is a longitudinal cross-sectional view of the cultural collection instrument in accordance with the present invention showing the extension of the swab or cultural collection element and the inner tubular swab protector element beyond the distal end of the culture collection instrument during culturing of the animal;

FIG. 5 is a fractional cross-sectional view of the cultural collection device showing the withdrawal outwardly of the inner tubular swab protector element containing the swab or cultural collection element from the outer sheath protector housing in accordance with the present invention;

FIG. 6 is a fractional cross-sectional view of the inner tubular swab protector element having a swab element or culture collection element contained therein with the distal end capped and sealed in accordance with the present invention;

FIG. 7 is a fractional cross-sectional view of the inner swab protector element illustrating flexing of the inner tubular swab protector element at the scored portion thereof to separate the end portion of the inner tubular swab protector element and the swab element contained therein to provide a tubular enclosure for the swab or cultural collection element in accordance with the present invention; and FIG. 8 is a longitudinal cross-sectional view of the separated tubular enclosure of the invention of FIG. 7 with both ends thereof capped to provide a sealed and sanitary holder for the swab element in accordance with the present invention.

DETAILED DESCRIPTION

Referring now to the drawings wherein like numerals have been used throughout the several views to designate the same or similar parts, there is shown in FIGS. 1 and 2 a culture collection instrument 10 which is comprised of an outer tubular sheath protector housing 11, an inner tubular swab protector element or tube 12, an inner tubular swab holder element 13, and an elongated rod member 17 slidably movable therein and having a swab element 14 extending beyond the distal end 17a of the inner tubular swab holder element 13 and a shield protector element 15 mounted on the distal end 16 of the outer sheath protector housing 11.

The outer tubular sheath protector housing 11 includes a shield protector element 15 sealingly attached to the distal end 16 thereof with the shield protector element composed of a soft vinyl material which is sealingly mounted to the outside surface of the outer tubular sheath protector 11. The specific construction and operation of the shield protector element 15 is fully described in my copending application Ser. No. 371,208.

As shown in FIGS. 2, 3 and 4, the cultural collection instrument 10 includes an inner tubular swab protector element 12 having a flange 19 at one end thereof, with the inner tubular swab protector element adapted for movement relative to the outer tubular sheath protector housing 11. The inner tubular swab holder element 13 is slidably positioned within the inner tubular swab protector element 12 and adapted for relative movement with respect to the inner tubular swab protector element. A swab element or member 14 is attached to an elongated rod 17, positioned within the swab holder element 13, which rod is adapted for relative movement with respect to the inner tubular swab holder element. Importantly, as best shown in FIGS. 5 and 6, the inner tubular swab protector element 12 includes a scored portion 20 thereon intermediate the end 12a and flange 19 thereof which provides, upon the flexing of the inner tubular swab protector element 12 and the inner tubular swab holder element 13, a predetermined breaking of the protector element 12, as will hereinafter be described.

When the cultural collection instrument 10 is fully inserted into the cervix of an animal (not shown), the inner tubular swab protector element 12 is moved forwardly to engage the shield protector element 15, which has a scored closed end portion 15a, which snaps open or breaks away upon engagement by the distal end 12a of the inner tubular swab protector element 12, as shown in FIG. 3. The operation of the shield protector element is fully disclosed in my copending application Ser. No. 371,208. The swab element 14 and elongated rod 17 are pushed forwardly into the cervix of the animal to either culture or apply medication to the animal, as desired, the position as shown in FIG. 4.

Upon completion of the culturing or medication processes, the inner tubular swab holder element 13 and the elongated rod 17 and the swab element 14 thereon are moved outwardly or withdrawn from the cervix relative to the outer sheath protecting housing 11, the position as approximately shown in FIG. 3. Further withdrawal of the inner tubular swab holder 13, elongated rod 17 and swab element 14, and inner tubular swab protector element 12 completely encloses the swab holder 13 and swab element 14 within the instrument, the position as shown in FIG. 2 and the cultural collection instrument 10 is then removed from the animal.

The inner tubular swab protector element 12, containing the inner tubular swab holder 13, elongated rod 17 and the swab element 14 is withdrawn from the outer sheath protector housing 11, the postion as partially shown in FIG. 5.

An end cap 21 is inserted upon the distal end 12a of the inner tubular swab protector element 12, the position as shown in FIG. 6, to seal one end of the protector element 12. Thereafter, the inner tubular swab holder element, the elongated rod and swab element 14 are further withdrawn such that the distal end 22 of the inner tubular swab holder element 13 is moved outwardly beyond the scored portion 20 of the inner tubular swab protector element 12, the postion as shown in FIG. 7.

Upon the manual flexing of the inner tubular swab protector element or tube 12, the protector element 12 readily and predeterminely breaks and separates at the scored portion thereof and readily breaks the elongated rod 17 which extends through the inner tubular swab holder 13, the position as shown in FIG. 7. By scoring, it is meant that the protector element 12 may have a notch or indentation either partially or completly therearound, which will permit a complete breaking and separation of the protector element upon manual flexing. Upon the predetermined breaking of the swab protector element 12, an end cap 24 is inserted upon the end of the swab protector element or tube 12 opposite the distal end 12a thereof to provide a tubular sealed enclosure which provides a sealed and sanitary holder for the cultured swab element which permits subsequent handling of the cultured swab element prior to medical testing of the element, as shown in FIG. 8.

It has been determined that the composition of the elongated rod 17 may generally be of a soft plastic material which readily breaks when the inner tubular swab protector element 12 is manually flexed. However, it is within the scope of the present invention that the tubular rod may also be scored, as shown by numeral 26 in FIGS. 6 and 7. However, it is preferred that the rod 17 be composed of a soft plastic material such that scoring of the elongated rod is not necessary to provide a sealed and sanitary tubular holder for the swab element to permit subsequent handling and transport for mechanical testing of the cultured swab element.

Although the drawings illustrate the swab element attached to an elongated rod 17 which is slidable and movable within the tubular swab holder element 13, it is within the scope of the present invention that the swab element 14 may be firmly attached to the end 22 of the swab holder element 13 and the swab element 14 is mounted to and extends forwardly of the end 22 of swab holder element 13 by a portion of the rod 17b, as shown by dotted numeral 17a in FIGS. 5 and 6. In such an embodiment, the rod 17 will terminate adjacent the end 22 of the swab holder element 13 and the forward and withdrawal movement of the swab element 14 will be accomplished by movement of the swab holder element 13 extending rearwardly of the flange 19.

Additionally, it is further within the scope of the present invention that the swab element 14 and the elongated rod 17 may be properly sized with respect to the interior diameter of the tubular swab protector element 12, such that the culture collection instrument 10 does not include a tubular swab holder element 13. In such an embodiment, the elongated rod 17 extends beyond the flange 19 on the tubular swab protector element 12 and the instrument 10 would appear as shown in the drawings except that the instrument would not include a swab holder element 13. In such an embodiment, manual flexing of the inner tubular swab protector element or tube 12, predeterminely breaks and separates at the scored portion 20 thereof and readily breaks the elongated rod 17 to provide a tubular enclosure having the cultured swab element 14 therein, as shown in FIG. 8, and which has heretofore been described.

Thus while I have illustrated and described the preferred embodiments of my invention, it is to be understood that this is capable of variation and modification, and I, therefore, do not wish to be limited to the precise details set forth but desire to avail myself of such changes and alterations as fall within the purview of the following claims.

I claim:

1. A culture collection instrument for culturing of an animal including in combination;
   an elongated rod having a swab element mounted on the end thereof;
   an inner tubular swab holder element adapted to receive said elongated rod and permit relative movement therebetween;
   an inner tubular swab protector element adapted to receive said inner tubular swab holder element and adapted for relative movement therebetween, an outer tubular sheath protector housing adapted to receive said inner tubular swab protector element and permit relative longitudinal movement therebetween, and a shield protector element mounted to the distal end of said outer tubular sheath protector housing and wherein said closed end portion of said shield protector element is scored to provide a break away membrane when said closed end of the shield protector is engaged by the end of said inner tubular swab protector element;
   wherein said inner tubular swab protector element includes a scored portion thereof intermediate the ends thereof which permits a predetermined breaking of said inner tubular swab protector element and said swab element from said elongated rod to provide a tubular holder for the culture swab element; and
   capping means engageable with said ends of said tubular holder defined by said protector element to provide a sealed and sanitary holder for the cultured swab element.

2. The culture collection instrument in accordance with claim 1 wherein said elongated rod is scored to permit a predetermined breaking of said swab element therefrom during the predetermined breaking of said inner tubular swab protector element.

3. The culture collection instrument in accordance with claim 1 wherein said scored portion on said inner tubular swab protector element is completely around said inner tubular swab protector element.

4. A culture collection instrument for inserting into the cervix of an animal for culturing of an animal including in combination;
   an elongated rod having a swab element mounted on the end thereof;
   an inner tubular swab protector element adapted to receive said elongated rod and said swab element thereon and adapted for relative movement therebetween;
   an outer tubular sheath protector housing adapted to receive said inner tubular swab protector element and permit relative longitudinal movement therebetween, and a shield protector element mounted to the distal end of said outer tubular sheath protector housing and wherein said closed end portion of said shield protector element is scored to provide a break away membrane when said closed end of the shield protector is engaged by the end of said inner tubular swab protector element when the instrument is inserted into the cervix of the animal;
   wherein said inner tubular swab protector element includes a scored portion thereof intermediate the ends thereof which permits a predetermined breaking of said inner tubular swab protector element and said swab element from said elongated rod to provide a tubular holder for the cultured swab element; and
   capping means engageable with both of said ends of said tubular holder defined by said protector element to provide a sealed and sanitary holder for the cultured swab element.

5. The culture collection instrument in accordance with claim 4 wherein said elongated rod is scored to permit a predetermined breaking of said swab element therefrom during the predetermined breaking of said inner tubular swab protector element.

6. The culture collection instrument in accordance with claim 4 wherein said scored portion on said inner tubular swab protector element is completely around said inner tubular swab protector element.

7. A culture collection instrument for culturing of an animal including in combination;
   an inner tubular swab holder element having a distal end and a swab element mounted to and extending beyond the distal end of said inner tubular swab holder element;
   an inner tubular swab protector element adapted to receive said inner tubular swab holder element and said swab element thereon and adapted for relative movement therebetween, an outer tubular sheath protector housing adapted to receive said inner tubular swab protector element and permit relative longitudinal movement therebetween, and a shield protector element mounted to the distal end of said outer tubular sheath protector housing and wherein said closed end portion of said shield protector element is scored to provide as break away membrane when said closed end of the shield protector is engaged by the end of said inner tubular swab protector element;

wherein said inner tubular swab protector element includes a scored portion thereof intermediate the ends thereof which permits a predetermined breaking of said inner tubular swab protector element and said swab element from said distal end of said inner tubular swab holder element to provide a tubular holder for the cultured swab element; and capping means enageable with said ends of said tubular holder defined by said protector element to provide a sealed and sanitary holder for the cultured swab element.

8. The culture collection instrument in accordance with claim 7 wherein said swab element is scored to permit a predetermined breaking of said element mounted to said distal end of said inner tubular swab holder element during the predetermined breaking of said inner tubular swab protector element.

9. The culture collection instrument in accordance with claim 7 wherein said scored portion on said inner tubular swab protector element is completely around said inner tubular swab protector element.

* * * * *